United States Patent
Sciutto Conde et al.

(10) Patent No.: US 9,446,122 B2
(45) Date of Patent: Sep. 20, 2016

(54) USE OF GK-1 PEPTIDE EXPRESSED ON M13 FILAMENTOUS PHAGE AS PHARMACEUTICAL INGREDIENT TO ENHANCE THE EFFICIENCY OF THE IMMUNE RESPONSE INDUCED BY VACCINE OR PATHOGEN ANTIGENS

(75) Inventors: Edda Lydia Sciutto Conde, Morelos (MX); Gladis del Carmen Fragoso Gonzalez, Mexico City (MX); René Alvaro Segura Velázquez, Mexico City (MX); Jacquelynne Brenda Cervantes Torres, Mexico City (MX); Karen Manucharyan, Mexico City (MX); Abel Blancas Cabrera, Mexico City (MX); Rutilia Marisela Hernandez Gonzales, Mexico City (MX)

(73) Assignee: UNIVERSIDAD NACIONAL AUTONOMA DE MEXICO, Mexico City (MX)

( * ) Notice: Subject to any disclaimer, the term of this patent is extended or adjusted under 35 U.S.C. 154(b) by 0 days.

(21) Appl. No.: 14/234,983

(22) PCT Filed: Jul. 28, 2012

(86) PCT No.: PCT/MX2012/000071
§ 371 (c)(1),
(2), (4) Date: May 5, 2014

(87) PCT Pub. No.: WO2013/015668
PCT Pub. Date: Jan. 31, 2013

(65) Prior Publication Data
US 2014/0302085 A1 Oct. 9, 2014

(30) Foreign Application Priority Data
Jul. 26, 2011 (MX) .................. MX/A/2011/007874

(51) Int. Cl.
| | | |
|---|---|---|
| A61K 39/40 | (2006.01) |
| A61K 39/39 | (2006.01) |
| A61K 39/145 | (2006.01) |
| A61K 38/10 | (2006.01) |
| C12N 7/00 | (2006.01) |
| A61K 39/12 | (2006.01) |
| C07K 14/435 | (2006.01) |
| A61K 39/00 | (2006.01) |

(52) U.S. Cl.
CPC ............. *A61K 39/39* (2013.01); *A61K 38/10* (2013.01); *A61K 39/12* (2013.01); *A61K 39/145* (2013.01); *C07K 14/43554* (2013.01); *C12N 7/00* (2013.01); *A61K 2039/543* (2013.01); *A61K 2039/55516* (2013.01); *A61K 2039/70* (2013.01); *C07K 2319/735* (2013.01); *C12N 2760/16134* (2013.01); *C12N 2760/16234* (2013.01)

(58) Field of Classification Search
None
See application file for complete search history.

(56) References Cited

FOREIGN PATENT DOCUMENTS

| | | |
|---|---|---|
| MX | PA00008474 A | 1/2004 |
| MX | PA05003413 A | 2/2007 |

OTHER PUBLICATIONS

Segura-Velazquez et al. (Vaccine vol. 24, pp. 1073-1080, 2006).*
Machine Translation of Conda Mexican application.*
Fargoso et al., Clinical and Vaccine Immunology, vol. 18, No. 7 pp. 1067-1076 published ahead of print on May 18, 2011.*
Rene Segura-Velazquez, et al. "Towards Identification of the Mechanisms of Action of Parasite-Derived Peptide GK1 on the Immunogenicity of an Infuenza Vaccine" Clinical and Vaccine Immunology, Sep. 2009, p. 1338-1343.
Karen Manoutcharian, et al. "Recombinant bacteriophage-based multiepitope vaccine against Taenia Solium pig cysticercosis" Veterinary Immunology and Immunopathology, 2004, vol. 99, pp. 11-24.

* cited by examiner

*Primary Examiner* — Gary Nickol
*Assistant Examiner* — Khatol Shahnan Shah
(74) *Attorney, Agent, or Firm* — Lucas & Mercanti, LLP

(57) ABSTRACT

The present invention is directed to the use of FGK-1 immunopotentiator, composed by the peptide named GK-1, characterized by the sequence G-Y-Y-Y-P-S-D-P-N-T-F-Y-A-P-P-Y-S-A (SEQ ID No. 1) and linked to the pVIII surface protein of M13 filamentous phage, to prepare pharmaceutical products potentiating the protective immune response of vaccine antigens when used by itself or conjointly with these antigens administered either intranasally, subcutaneously, or intramuscularly, yielding an increase in the level of specific antibodies against vaccine antigens in serum and in bronchioalveolar lavages.

5 Claims, 7 Drawing Sheets

USE OF GK-1 PEPTIDE EXPRESSED ON M13 FILAMENTOUS PHAGE AS PHARMACEUTICAL INGREDIENT TO ENHANCE THE EFFICIENCY OF THE IMMUNE RESPONSE INDUCED BY VACCINE OR PATHOGEN ANTIGENS

CROSS-REFERENCE TO RELATED APPLICATIONS

This application is a 371 of PCT/MX2012/000071 filed Jul. 28, 2012, which in turn claims the priority of MX/a/2011/007874 filed Jul. 26, 2011, the priority of both applications is hereby claimed and both applications are incorporated by reference herein.

FIELD OF THE INVENTION

The present invention is directed to the use of FGK-1 as immunopotentiator, enhancing the efficiency of the immune response induced by viral antigens or virus-based vaccine antigens. FGK-1 is composed by the peptide called GK-1, linked to M13 filamentous phage as a phagemid to potentiate the immunoprotector capacity elicited by several vaccines, as well as to improve the immune response aimed to control the establishment and development of different pathogens.

BACKGROUND OF THE INVENTION

The efficiency of immune response against different pathogens, either induced by vaccination or by contact with the pathogen itself, depends on a number of complex phenomena, such as, antigen presentation by professional presenter cells, specific lymphocyte activation, cell differentiation, antibody production, and other humoral factors mediating cell communication. The underlying complexity of the immune response mechanisms is a rationale for the heterogeneous efficiency in controlling different infections or vaccine-induced responses. It is feasible that those phenomena determining the induction of acquired immunity may be enhanced by potentiating the antigen presentation phenomenon, a critical phase for inducing an effective immune response. The use of adjuvants has been relevant especially to potentiate vaccines with poor protector capacity, like influenza vaccine for instance.

There is a number of immunopotentiators or adjuvants in the state of the art, like aluminum hydroxide or phosphate. This adjuvant was first reported in 1926, and was the first authorized for human use. However, it bears some limitations, especially by inducing a strong T cell-mediated immune response [Chang S. et al. 2009], which is counter-producing instead of favorable in certain treatments. Additionally, aluminum hydroxide specifically exacerbates a cellular response, which is not adequate to prevent certain diseases where protection is particularly associated to the humoral immune response.

Another adjuvant used in human vaccines is described on EP0399843B1, a water-in-oil emulsion with squalene, known as MF59, which is used in combination with influenza vaccine. While this adjuvant has increased the humoral immune response when parenterally co-administered with the vaccine, the immunoenhancing effect of MF59 is limited in high-risk age groups, and the vaccine exhibits a poor efficiency in those groups. Another limitation of MF59 adjuvant is that its effectiveness has been demonstrated only when administered parenterally. MF59 has not shown any potentiating effect in the vaccine response when intranasally or orally administered [Boyce T G et al. 2000].

MF59 only potentiates the production of IgG-class antibodies, and when co-administered with influenza vaccine to the higher-risk groups it fails to induce a protection as efficient as the one it elicits when administered to younger individuals. Additionally, MF59 enhancer effect is limited to the parenteral route of administration for the vaccine.

In the state of the art, patent MX270782 describes GK-1 peptide as SEQ ID No. 1, an 18-amino acid sequence G-Y-Y-Y-P-S-D-P-N-T-F-Y-A-P-P-Y-S-A derived from a *Taenia solium* cysticerci cDNA library; it contains at least a B-cell epitope and a T-cell epitope capable of stimulating CD8+ and CD4+ proliferation. Additionally, it has been observed that supernatant of cells specifically stimulated with this peptide contains high IFN-γ levels, as well as IL-2 and in a lesser degree IL-4. Similar results were obtained when cytokine production was measured in T-cells by flow cytometry, which points to the peptide capacity to promote an inflammatory response [Toledo A et al. Infection Immun 1999; 67 (5): 2522-30].

GK-1 peptide is capable by itself of enhancing the activation state of cells participating in antigen presentation (macrophages and dendritic cells). When administered conjointly with vaccine antigens, GK-1 has showed to increase the vaccine-induced protective immune response, measured in terms of the amount of produced antibodies and the recovered viral titer after challenge.

On patent MX228767, M13 filamentous phage is described as having the capacity of exacerbating the specific immune response when administered subcutaneously or intranasally.

On Manoutcharian K et al. Vet Immunol Immunopathol 2004; 99: 11-24, the protective capacity against murine and porcine cysticercosis of CPhV vaccine, composed by recombinant phages KETc1, KETc12, GK1, and KETc7 ($4 \times 10^{12}$ phage particles), is described. It was shown that CPhV elicits a specific cellular immune response, but not a humoral one.

On Morales J et al. Vaccine 2008; 26: 2899-2905, the phagemid is revealed as a component of the recombinant vaccine against cysticercosis named S3Pvac-phage.

On Morales J et al. Vet Parasitol 2011; 176: 53-58, the capacity of S3Pvac-phage vaccine to reduce the prevalence of cysticercosis (caused by *Taenia solium*) and hydatidosis (caused by the tapeworm *Echinococcus granulosus*) in pigs is described. This effect is due to the cross-reactivity given the high homology of the vaccine components in both cestodes.

DESCRIPTION OF THE INVENTION

The present invention is directed to a new usage of FGK-1 as immunopotentiator, increasing the immune response induced by virus-based vaccine antigens. FGK-1 is a phagemid expressing the GK-1 peptide on its surface, where GK-1 is linked to pVIII protein of M13 filamentous phage. More specifically, but not limiting the present invention in any way, it is directed to the usage of FGK-1 as immunopotentiator, aiding the action of several protective vaccines against influenza virus.

The performance of FGK-1 immunopotentiator in the present invention has been tested with influenza vaccine in an illustrative, but not limitative way. It has been proved as capable of inducing a higher humoral response in different age groups of mice, including mice older than 18 months. The latter mouse group models one of the human population groups with higher risk of morbi-mortality by influenza.

Moreover, it is worth noting that FGK-1 has been shown to potentiate antibody production, both in serum and in bronchoalveolar lavages, and both IgG and IgA classes, being the latter relevant in mucosal protection.

On the other side, studies performed on syngeneic mice using FGK-1 as adjuvant for influenza vaccine have shown that subcutaneously co-administering FGK-1 and influenza vaccine yields a higher response of anti-influenza specific antigens than that induced in equivalent conditions by influenza vaccine conjointly with MF59. An antibody increase is observed both in IgG and in IgA classes, and both in serum and in bronchoalveolar lavages.

Apart from obtaining a higher humoral response when immunizing subcutaneously, when using intranasally the influenza vaccine conjointly with FGK-1, higher antibody levels are observed, both in IgG and in IgA subtypes, and both in serum and in bronchoalveolar lavages. These results raise the interest of including FGK-1 in new versions of oral or intranasal vaccines, representing a clear advantage over MF59, which does not show this capacity.

By immunizing mice either parenterally or intranasally with influenza vaccine, in presence or not of M13 or FGK-1, and measuring the levels of induced antibodies in serum and in bronchoalveolar lavages, it has been observed that both M13 and FGK-1 increase the expected local and systemic antibody levels with respect to those induced by immunization with the vaccine by itself. However, antibody response in both compartments is significantly higher when the influenza vaccine is co-administered with FGK-1 than with M13 alone.

While M13 and GK-1 themselves enhance the immune response, merging M13 and GK-1 to form FGK-1 has shown a synergic effect in enhancing the immune response when co-administered with vaccines; therefore, it is not possible to deduce this from the nearest state of the art.

Similarly, synthetic GK-1 peptide has been shown, when co-administered with influenza vaccine, to potentiate the vaccine-induced protective response in an influenza model of younger and older mice; the latter mouse group models human population older than 65 years, a group with higher risk of morbi-mortality by influenza. In spite of potentiating the protective response in both population age groups when co-administered with influenza vaccine, synthetic GK-1 peptide does not increase antibody levels in younger mice with respect to those induced by the vaccine alone. In contrast, co-administration of FGK-1 with influenza vaccine increases antibody levels by over 60% both in younger and in older mice, demonstrating the higher potentiating capacity of FGK-1 versus synthetic GK-1.

FGK-1 further exhibits, with respect to synthetic GK-1, the capacity of immunopotentiating the influenza vaccine when intranasally administered. Synthetic GK-1 does not potentiate the vaccine by intranasal administration.

On the other side, it has been shown that, when co-administered with the commercial influenza vaccines FLUZONE® (adjuvant-free) and FLUAD® (including MF59 adjuvant in its formula), S3Pvac-phage elicits an immune response comparable to that elicited by commercial vaccines. This indicates that S3Pvac-phage lacks the capacity of immunopotentiating the antibody response induced by commercial influenza vaccines with or without adjuvant, as the use of FGK-1 with both vaccines does.

Finally, the effectiveness of FGK-1 in potentiating local and systemic antibody response as demonstrated using the influenza vaccine strongly suggests its usefulness as adjuvant to potentiate the response induced by different vaccines.

Another advantage is the FGK1 lower production cost and the stability of the phage-expressed product. It has proved to retain its efficacy one year after production, at least.

An additional benefit of FGK-1 over synthetic GK-1 is the difference in production costs. Recombinant production of FGK-1 is less expensive than the peptide full synthesis.

FGK-1, immunopotentiator of the present invention, is composed by an 18-amino acid sequence G-Y-Y-Y-P-S-D-P-N-T-F-Y-A-P-P-Y-S-A (SEQ ID No. 1) linked to the pVIII protein on the surface of M13 filamentous phage; the scope of the present invention encompasses the capacity of FGK-1 to potentiate vaccines. On this basis, FGK-1 is useful as pharmaceutical ingredient to be administered by itself or co-administered with the vaccine to be potentiated, resulting in that FGK-1 potentiates the immune response in mammals and birds against different antigenic components of the respective virus-based vaccines, either being live, attenuated, or inactivated vaccines, or constituted by native, synthetic, or recombinant antigens, either for human or veterinary use.

Intranasal, subcutaneous, or parenteral administration of pharmaceutical products including vaccines plus FGK-1 in their formulae to mammals results in potentiating the vaccine-induced immune response, increasing specific antibody production, particularly IgA and IgG subtypes, against the corresponding vaccine antigens. With regard to the cellular immune response, an enhancement of antigen presentation by antigen-presenter cells is elicited, thus favoring the eradication of different pathogens.

EMBODIMENTS OF THE INVENTION

The object of the invention is to provide a new usage to FGK-1 as immunopotentiator, since when co-administered with a vaccine it potentiates the immune response both in mammals, including humans, and in birds, applicable to any age group.

Part of the embodiments of the invention are any pharmaceutical compositions comprising FGK-1 and different vaccine antigens, either forming a single composition or as individual compositions, or even a pharmaceutical product in the form of a kit comprising the FGK-1 pharmaceutical composition and different vaccine antigens.

It is a preferred embodiment of the invention the usage of FGK-1 as immunopotentiator to augment the immune response and favor the immunity induced by administering different vaccine antigens.

The invention encompasses the possibility of indicating that the pharmaceutical components a) FGK-1 and b) different vaccine antigens are appropriate for administration to a patient by any route, although the preferred administration routes are parenteral (subcutaneous or intramuscular) and nasal.

One embodiment of the invention is related to the usage of FGK-1 as immunopotentiator for the influenza vaccine, aimed to augment the production of specific antibodies, as detected in the patient serum according to a standardized protocol and with the appropriate doses.

A part of this embodiment is related to the possibility of augmenting the production of specific IgG antibodies, as detected in serum, when the vaccine and FGK-1 are administered intranasally, showing increases from 229% through 288%; or to augment at least by 30% the production of specific IgG antibodies, as detected in serum, when FGK-1 and the influenza vaccine are co-administered by subcutaneous route.

Another part of this embodiment of the invention is related to the usage of FGK-1 as immunopotentiator for the influenza vaccine to augment the production of serum induced IgA antibodies when FGK-1 and the vaccine are co-administered intranasally, from 37% through 54%; or to augment at least by 20% the production of serum induced IgA antibodies when FGK-1 and the influenza vaccine are co-administered by subcutaneous route.

Another embodiment of the invention is related to the usage of FGK-1 as immunopotentiator for the influenza vaccine, augmenting by up to 280% the levels of antibodies of IgA class detected in bronchoalveolar lavages when FGK-1 and the vaccine are co-administered intranasally.

Another embodiment of the invention is related to the clinical usage of the pharmaceutical product encompassed by the invention, when administered according to an immunization protocol designed by the medical doctor expert in infectious diseases, immunologist, and/or epidemiologist, or a related field specialist, which is singled out precisely for using FGK-1 co-administered with a vaccine, to a patient requiring it.

FGK-1 immunopotentiator can be administered by itself and sequentially to the vaccine to be potentiated, or co-administered with the vaccine to be potentiated by intranasal, subcutaneous, or parenteral route.

FGK-1 immunopotentiator can be included in vaccine formulae, to potentiate their protective capacity when administered to mammals intranasally or by parenteral route (subcutaneous or intramuscular).

EXAMPLES

Figure 1:
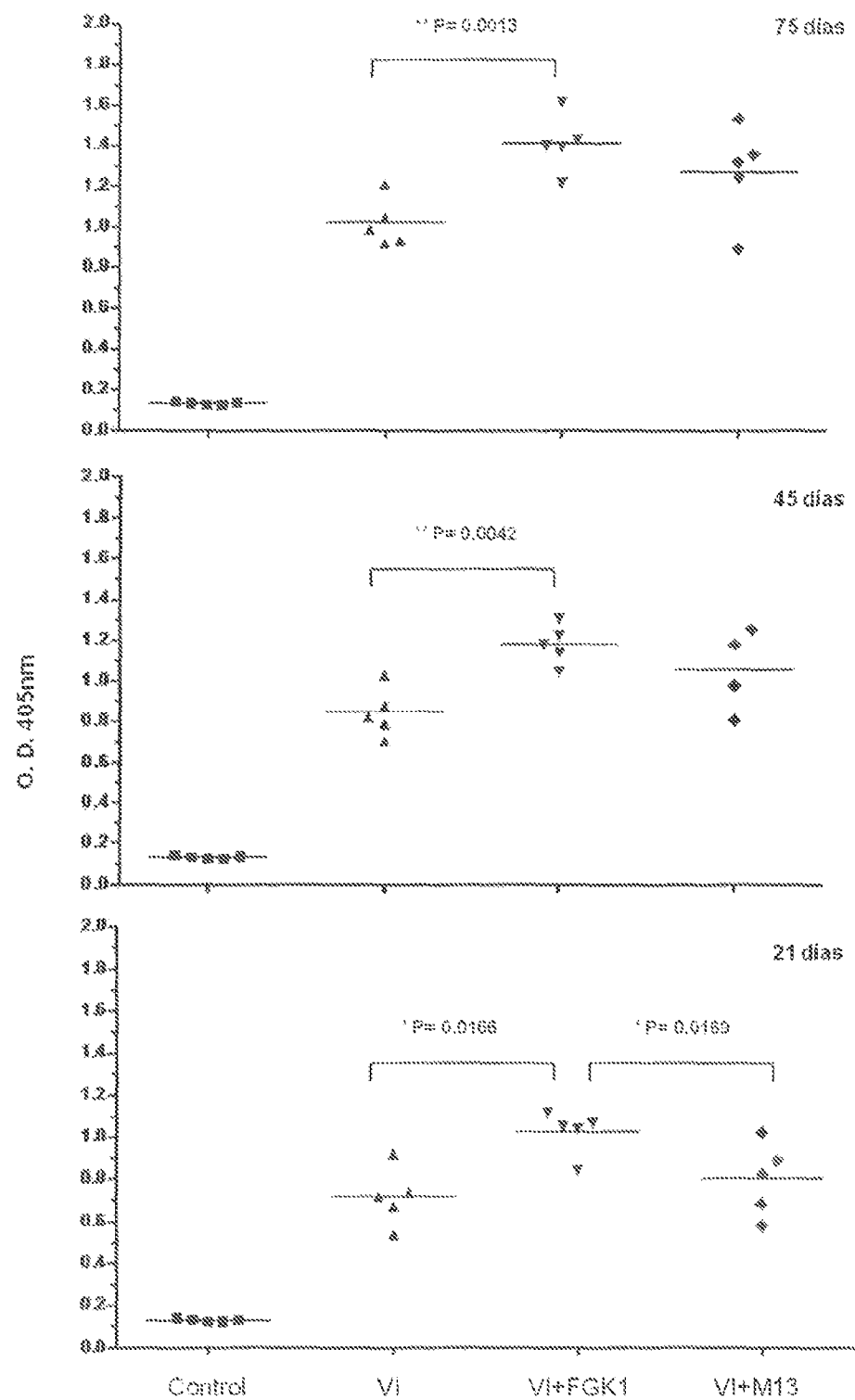
FIG. 1 shows blood antibody (IgG) levels in three different times after immunization (21, 45, and 75 days) induced by subcutaneously immunizing female BALB/cAnN mice with: 1. Saline solution (negative control); 2. Human influenza vaccine (IV) FLUZONE®; 3. FGK-1 plus Human influenza vaccine (IV) FLUZONE®, and 4. Human influenza vaccine (IV) FLUZONE® plus M13.

The following examples are aimed to illustrate the invention, but are in no way limitative on the invention.

Example 1

Constructing the Gk-1 Phage Expressed on M13 Filamentous Phage (FGK-1)

To construct FGK-1, the GK-1 peptide was used; GK-1 was reported in the patent MX211604, which refers to the capacity of this peptide to enhance antigenic presentation, a phenomenon that mediates the vaccine-induced specific immune response. Additionally, an expression system called M13 was used; M13 was reported in the patent MXPA00008474A, which refers to the capacity of M13 to express vaccine antigens.

To perform the studies supporting the present invention, GK-1 peptide was recombinantly expressed.

GK-1 peptide is the sequence of amino acids 69-85 in the KETc7 antigen, and its specific sequence is GYYYPSD-PNTFYAPPYSA (SEQ ID No. 2). It was expressed on the surface of M13 phage by cloning the corresponding DNA in the phage/phagemid vector. The DNA fragment coding for GK-1 peptide was generated by aligning the synthetic oligonucleotides (Invitrogen) 5'GK1: AATTAGGTTATTAC-TATCCTATCTGATCCAAATACCTTCTACGCTCCAC-CCTACAGC (SEQ ID No. 3) and 3'GK1: GATCGCTGTAGGGTGGAGCGTAGAAGGTATTTG-GATCAGATGGATAGTAATAACCT (SEQ ID No. 4), which contain the restriction sites EcoRI and BamHI. Then, DNA was digested with EcoRI/BamHI, the GK-1 fragment was purified from the agarose gel and precipitated in ethanol.

The correct amino acid sequence in GK-1 peptide associated to pVIII surface proteins was confirmed both by automated and by manual sequencing. For automated sequencing, the AB1 Pris 310 sequencer (Applied Biosystems, Foster City, Calif.) was used, using specific primers. For manual sequencing, the genetic construct was verified by sequencing using [$\alpha$-35S] dATP (Amersham-Life Science) and Quick-Denature plasmid sequencing kit (Amersham).

The FGK-1 construct was titrated to determine the phagemid titer in culture supernatants. TG1 cells were grown overnight in 10 ml of 2×YT medium (Invitrogen) at 37° C. and 200 rpm. Infection was performed in microtubes with 200 µl of TG1 cells and 50 µA of dilution supernatant ($10^{-9}$ to $10^{-11}$) in 2× YT medium. Tubes were incubated during 30 min at 37° C. without agitation, and the whole volume was poured on LB ampicillin boxes (100 µg/ml), incubated overnight at 37° C., and the number of colony forming units per ml (CFU/ml) was determined for each supernatant.

Example 2

Determining the Effect of FGK-1 in Improving the Immune Response

To assess the effect of FGK-1 in improving the immune response elicited by vaccine antigens, the levels of induced specific antibodies were determined. This parameter was used to evaluate the effect of FGK-1 on the immune response. With the aim to determine the FGK-1 immunopotentiating effect, different lots of influenza vaccine, produced between 2001 and 2009, were used.

In each experiment, groups of female BALB/cAnN mice, 7-9 weeks of age, were used in a number varying according to the test to be performed. Mice received either subcutaneously or intranasally one single dose of each immunogen. Mice were sacrificed 45 days after immunization. Blood samples were collected before immunization, as well as 21 and 45 days after immunization, and bronchoalveolar lavage was collected on day 45.

Treatment Schedules Used were as Follows:

A first group was immunized with PBS, to be considered as negative control group; the second group received influenza vaccine alone; the third group received influenza vaccine co-administered with FGK-1, and the fourth group was immunized with influenza vaccine plus M13 not expressing GK-1.

IgG and IgA antibody levels present in sera and bronchoalveolar lavages were determined by the ELISA technique. In the case of IgG, serum was used at a 1:100 dilution; to determine IgA in serum a 1:50 dilution was used, and to determine IgA and IgG in bronchoalveolar lavages undiluted samples were used. It was demonstrated that conjoint administration of the vaccine and FGK-1 construct, both intranasally and subcutaneously, increased in a very significant extent the serum specific antibody levels, both IgG and IgA with respect with those levels induced by the different vaccine lots employed. It was also demonstrated that co-administering FGK-1 and the influenza vaccine yields an increase in the antibody levels detected in bronchoalveolar lavages.

The data gathered from these experiments demonstrate that the FGK-1 construct can be used conjointly with vaccine antigens to enhance the protective immune response.

Example 3

Determining the Effect of FGK-1 to Enhance the Immune Response Elicited by Viral Influenza Vaccine To demonstrate the potentiating effect of FGK-1 on the immune response elicited by the influenza vaccine and to observe it at long times, four groups of female BALB/cAnN mice, 7-9 weeks of age, were used. The following treatment schedules were applied to the four groups:

Influenza vaccine was used at a dose of 1 µg/mouse [A/New Caledonia/20/99(H1N1) strain, A/Panama/2007/99 (H3N2) strain (analog to A/Moscow/10/99 strain), and B/Victoria/504/2000 strain (analog to B/Sichuan/379/99 strain)]. FLUZONE® vaccine for the flu season 2004-2005, containing 45 µg of hemagglutinin HA per 0.5 ml-dose, was used.

Mice received a single dose of each immunogen by subcutaneous route at the tail base, and the induced response was evaluated in serum after immunization, namely at 21, 45, and 75 days.

Sera were obtained from sampled peripheral blood, centrifuged at 5,000 rpm by 12 min, and aliquots were frozen until analysis.

As shown on FIG. 1, it is evident that co-immunization with the vaccine and FGK-1 significantly increases the level of serum IgG influenza-antigen specific antibodies with respect to those levels induced by the vaccine alone. This result is observed since early times after immunization (21 days after immunization) and is sustained during the 45 and 75 days after immunization. Furthermore, it is evident that the level of antibodies induced by FGK-1 administration is increased in the same mouse group as detection is performed in later times (15% higher and 19% higher between days 15 and 45 and between days 45 and 75, respectively).

Comparing the serum IgG antibody response detected induced by co-administering the influenza vaccine and FGK-1 versus antibody levels induced by co-administering the influenza vaccine and M13 (the phage not expressing GK-1), it can be noted that 21 days after co-administration with FGK-1 higher antibody levels are induced with respect to those induced by co-administration with M13. This higher antibody level becomes evident at 45 and 75 days after immunization, showing increases over 11% (FIG. 1).

In conclusion, co-immunization with influenza vaccine plus FGK-1 yields a significant increase in the specific antibody level against influenza with respect to those induced by the vaccine alone. This increase is sustained even after 75 days, and this shows that the immune response induced by human influenza vaccine is improved. Also, it becomes evident that FGK-1 acts as a better immunopotentiator than M13 not expressing GK-1, for the level of induced antibodies is always higher when co-immunizing with FGK-1.

Example 4

Determining the Response Induced by FGK-1 with Respect to the Response Induced by Synthetic GK-1 Peptide when Subcutaneously Immunized To demonstrate the potentiating effect of FGK-1 on the immune response elicited by influenza vaccine, and compare it to the immune response elicited by the influenza vaccine when co-administered with GK-1 synthetic peptide, five groups of female BALB/cAnN mice, 7-8 weeks of age, were used. The following treatment schedules were assessed for five-mouse groups:

Influenza vaccine was administered at a dose of 1 µg/mouse [A/New Caledonia/20/99(H1N1) strain, A/Panama/2007/99(H3N2) strain (analog to A/Moscow/10/99 strain), and B/Victoria/504/2000 strain (analog to B/Sichuan/379/99 strain)]. FLUZONE® vaccine for the flu season 2004-2005, containing 45 µg of hemagglutinin HA per 0.5 ml-dose, was used.

Synthetic GK-1 peptide was used at its optimal dose (Segura-Velázquez et al. 2006), in a 10 µg/mouse concentration.

FGK-1 and M13 were used at titers of $10^{12}$ phage units per mouse, after inactivation as described in this document.

Mice received a single dose of each immunogen by subcutaneous route at the tail base, and the induced response was evaluated in serum 21 days after immunization. Sera were obtained from peripheral blood, centrifuged at 5,000 rpm by 12 min, and aliquots were frozen until analysis.

Figure 2:
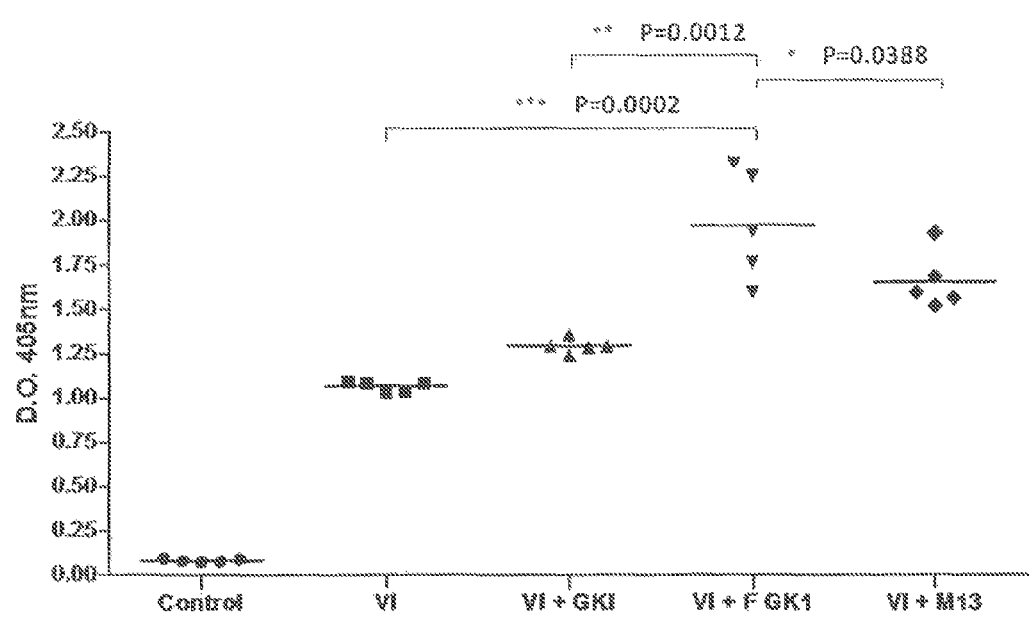
FIG. 2 shows the blood antibody (IgG) levels induced by subcutaneous immunization with: 1. PBS as negative control group; 2. Human influenza vaccine (IV) FLUZONE®; 3. Human influenza vaccine (IV) FLUZONE® plus synthetic GK-1; 4. Human influenza vaccine (IV) FLUZONE® plus FGK-1, and 5. Human influenza vaccine (IV) FLUZONE® plus M13. Antibodies were detected 21 days after immunization.

As shown on FIG. 2, co-immunization with influenza vaccine and synthetic GK-1 peptide induces a slightly higher antibody response with respect to that induced by influenza vaccine alone in mice regarded as younger, even though this increase is not statistically significant, a result already known (Segura-Velázquez et al. 2006). However, when comparing the antibody levels induced by immunization with influenza vaccine plus FGK-1, an increase in serum IgG antibody levels is observed, and it is significantly higher than those induced by influenza vaccine alone (85% higher), and also higher than those induced by immunization with influenza vaccine conjointly with synthetic GK-1 peptide (52% higher). When comparing the detected antibody levels after co-immunization with influenza vaccine and FGK-1, they are higher by 20% than those detected after co-immunization with influenza vaccine and M13.

In conclusion, these results demonstrate that expressing GK-1 in phage (FGK-1) and co-administering it with influenza vaccine induce a better immune response than that elicited by influenza vaccine, administered either alone or conjointly with synthetic GK-1 or with M13. This result becomes more evident by the higher induction of influenza-specific antibodies detected in serum after subcutaneous immunization.

Example 5

Determining the Response Induced by FGK-1 with Respect to the Response Induced by Synthetic GK-1 Peptide when Immunizing by Intranasal Route To demonstrate the potentiating effect of FGK-1 on the immune response elicited by intranasally administered influenza vaccine, and compare it to the immune response elicited by the influenza vaccine when co-administered with GK-1 synthetic peptide administered by the same route, seven groups of female BALB/cAnN mice, 7-8 weeks of age, were used. The following treatment schedules were administered to five-mouse groups:

Influenza vaccine was administered at a dose of 1 µg/mouse [A/New Caledonia/20/99(H1N1) strain, A/Panama/2007/99(H3N2) strain (analog to A/Moscow/10/99 strain), and B/Victoria/504/2000 strain (analog to B/Sichuan/379/99 strain)]. FLUZONE® vaccine for the flu season 2004-2005, containing 45 µg of hemagglutinin HA per 0.5 ml-dose, was used.

Synthetic GK-1 peptide was used at its optimal dose (Segura-Velázquez et al. 2006), in a 10 µg/mouse concentration.

Mice were administered intranasally one single dose of each immunogen, and the induced response was evaluated in serum and bronchoalveolar lavages in different times after immunization, namely 21 and 45 days. Sera were obtained from peripheral blood, centrifuged at 5,000 rpm by 12 min, and aliquots were frozen until analysis. Bronchoalveolar lavages were obtained by performing intratracheal lavages with 300 µl of saline solution 45 days after immunization.

FGK-1 Elicits a Higher IgG Response in Serum

Figure 3:
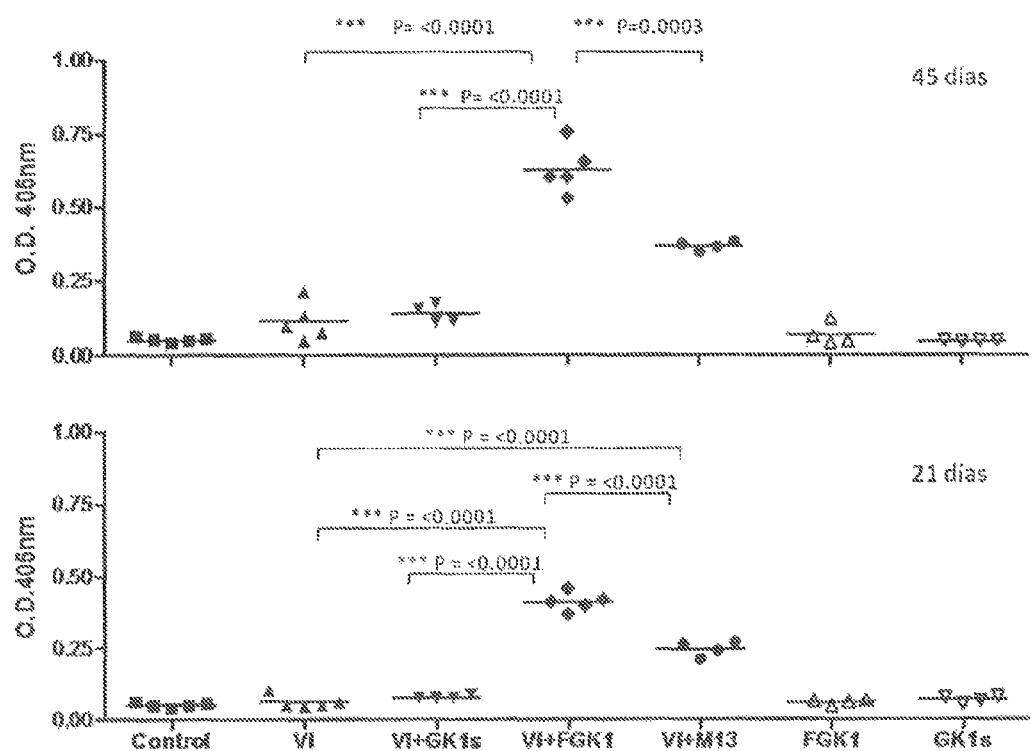
FIG. 3 shows the blood antibody (IgG) levels detected 21 and 45 days after intranasal immunization with the following treatments: 1. PBS as negative control group; 2. Human influenza vaccine (IV) FLUZONE®; 3. Human influenza vaccine (IV) FLUZONE® plus synthetic GK-1; 4. Human influenza vaccine (IV) FLUZONE® plus FGK-1; 5. Human influenza vaccine (IV) FLUZONE® plus M13; 6. FGK-1, and 7. Synthetic GK-1.

As shown on FIG. 3, FGK-1 induces a better immune response, as reflected in the induction of higher influenza antigen-specific IgG antibody levels detected in serum. When co-immunizing mice with influenza vaccine and FGK-1 by intranasal route, higher IgG antibody levels are elicited with respect to those induced when immunizing with influenza vaccine alone. This observation becomes evident at 21 days after immunization: at that time, antibody levels in a seven times higher proportion were obtained when mice were co-immunized with influenza vaccine and FGK-1 (a response 564% higher) with respect to those induced by influenza vaccine alone. Similarly, while detected IgG antibody levels when co-immunizing mice with influenza vaccine and M13 (the phage not expressing GK-1) are higher than those detected after immunizing mice with influenza vaccine alone 21 days after immunization, the immune response induced by co-immunization with FGK-1 and influenza vaccine is 66% higher than that induced by co-immunization with M13.

When comparing IgG levels detected in serum after intranasal immunization using either synthetic GK-1 or FGK-1 as adjuvant, it is evident that FGK-1 elicits higher serum antibody percentage (415%) than those induced with the other adjuvant.

At day 45 after immunization, IgG antibody levels detected in serum are higher than those detected at day 21 after infection and the differences among the immunized groups are sustained, and antibody levels are always higher in those groups immunized with influenza vaccine and FGK-1.

FGK-1 Improves IgG and IgA Response in Bronchoalveolar Lavages

Figure 4:
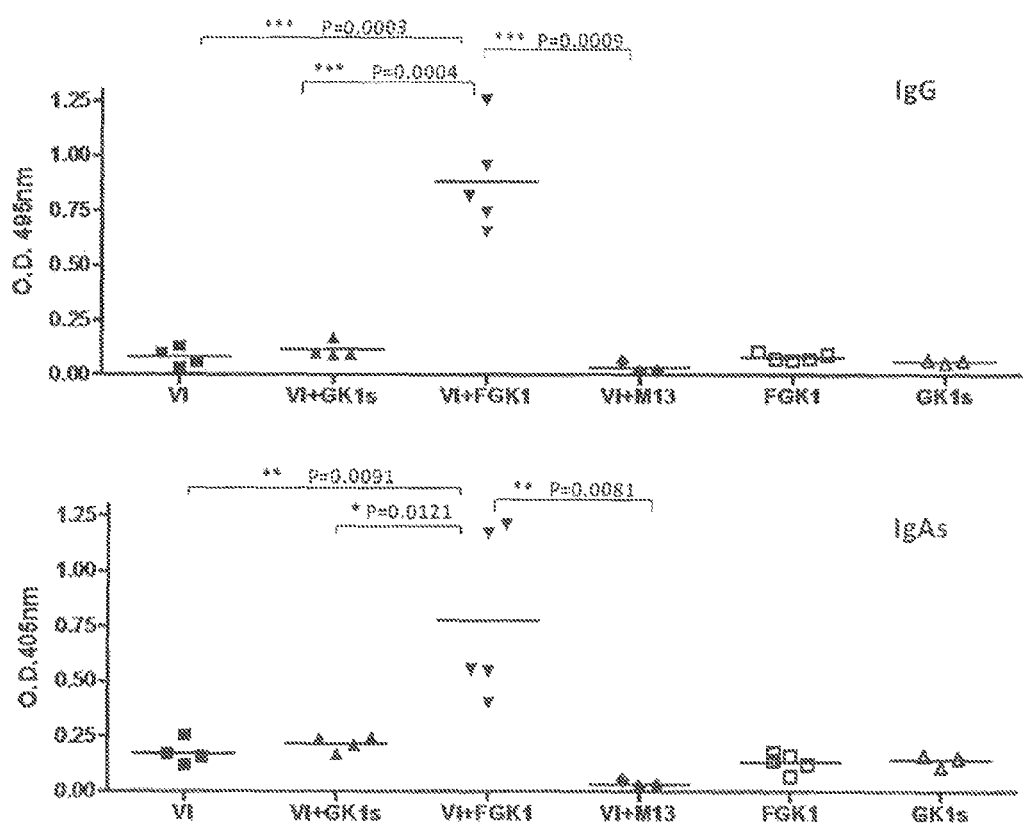
FIG. 4 shows antibody (IgG and IgA) levels in bronchoalveolar lavages detected 45 days after intranasal immunization with the following treatments: 1. Human influenza vaccine (IV) FLUZONE®; 2. Human influenza vaccine (IV) FLUZONE® plus synthetic GK-1; 3. Human influenza vaccine (IV) FLUZONE® plus FGK-1; 4. Human influenza vaccine (IV) FLUZONE® plus M13; 5. FGK-1, and 6. Synthetic GK-1.

As shown on FIG. 4, an influenza antigen-specific immune response could be elicited only in the groups co-immunized with influenza vaccine and FGK-1, expressed in the IgG and IgA antibody levels detected in bronchoalveolar lavages. With regard to induced IgG antibodies in bronchoalveolar lavages, this response was much higher than the response induced by the influenza vaccine alone. With regard to IgA antibodies detected in bronchoalveolar lavages, the group immunized with influenza vaccine and FGK-1 produced antigen levels four times higher than those induced in the group immunized with influenza vaccine (488% higher). In both instances, only the group receiving the vaccine and FGK-1 was able to exhibit a specific immune response.

Example 6

Determining the Effect of FGK-1 in Improving the Humoral Immune Response Elicited by Commercial Influenza Vaccine FLUZONE® and the Commercial Influenza Vaccine with Adjuvant FLUAD®

To evaluate the potentiating effect of FGK-1 on the antibody response elicited by two different types of commercial influenza vaccine, six groups of female BALB/cAnN mice, 6-7 weeks of age, were used. The following treatment schedules were evaluated:

FLUZONE® Influenza vaccine was administered at a dose of 1 µg/mouse [A/New Caledonia/20/99(H1N1) strain, A/Panama/2007/99(H3N2) strain (analogue to A/Moscow/10/99 strain), and B/Victoria/504/2000 strain (analogue to B/Sichuan/379/99 strain)]. FLUAD® influenza vaccine also at 1 µg/mouse [A/Brisbane/59/2007 (H1N1) strain (analogue to A/Brisbane/59/2007, IVR-148 strain), A/Brisbane/10/2007(H3N2) strain (analogue to A/Uruguay/716/2007, NYMC X-175C strain), and B/FLORIDA/4/2006 strain]. FLUZONE® vaccine for the flu season 2008-2009, containing 45 µg of hemagglutinins per 0.5 ml-dose, and FLUAD® vaccine for the flu season 2008-2009, containing 45 µg of hemagglutinins and MF59C.1 adjuvant per 0.5 ml-dose, were used.

FGK-1 and M13 were used at titers of $10^{12}$ phage units per mouse. Mice received a single dose of each immunogen by subcutaneous route at the tail base, and the induced response was evaluated in serum at different times after immunization, namely 21 and 45 days. Sera were obtained from peripheral blood, centrifuged at 5,000 rpm by 12 min, and aliquots were frozen until analysis.

Mice groups were segregated according to the immunization treatment they received, constituted in the following way:

One group was immunized with PBS only, regarded as negative control group. A second five-mouse group received adjuvant-free commercial influenza vaccine (FLUZONE®) only. The third five-mouse group received commercial influenza vaccine with adjuvant (FLUAD®). The fourth five-mouse group received adjuvant-free commercial influenza vaccine (FLUZONE®) co-administered with FGK-1. The fifth group received treatment with commercial influenza vaccine with adjuvant (FLUAD®) co-administered with FGK-1. Finally, the sixth five-mouse group received treatment with FGK-1 only.

Figure 5:
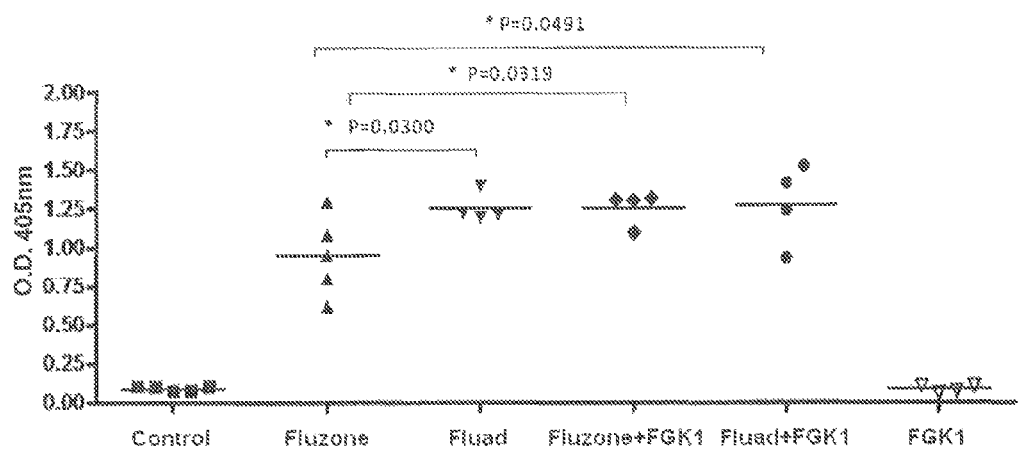
FIG. 5 shows the blood antibody (IgG) levels detected 21 days after immunization with the following treatments: 1. PBS as negative control group; 2. Human influenza vaccine FLUZONE®; 3. Human influenza vaccine FLUAD®; 4. Human influenza vaccine FLUZONE® plus FGK-1; 5. Human influenza vaccine FLUAD® plus FGK-1, and 6. FGK-1.

When co-administered with adjuvant-free commercial influenza vaccine (FLUZONE®), FGK-1 induces antibody levels similar to those induced by commercial vaccine with adjuvant (FLUAD®) in early times When determining the immune response induced by commercial influenza vaccines, deduced by comparing the specific IgG antibody levels in serum 21 days after immunization, FIG. 5 makes evident that commercial influenza vaccine containing MF59 adjuvant (FLUAD®) elicits a better antibody response than that induced by adjuvant-free commercial influenza vaccine FLUZONE®. However, when co-administering FGK-1 as adjuvant for FLUZONE® vaccine, an antibody response similar to that elicited by the commercial vaccine with adjuvant is observed.

When co-administered with adjuvant-free commercial influenza vaccine (FLUZONE®), FGK-1 induces a higher antibody response than that induced by commercial adjuvant-containing vaccine (FLUAD®), potentiating as well the antibody response induced by commercial adjuvant-containing vaccine At day 45 after administering the different treatments, the induced immune response (as deduced by induced IgG antibody levels detected in serum) was compared among both available types of commercial influenza vaccine (with or without adjuvant) administered either alone or conjointly with FGK-1.

Figure 6:
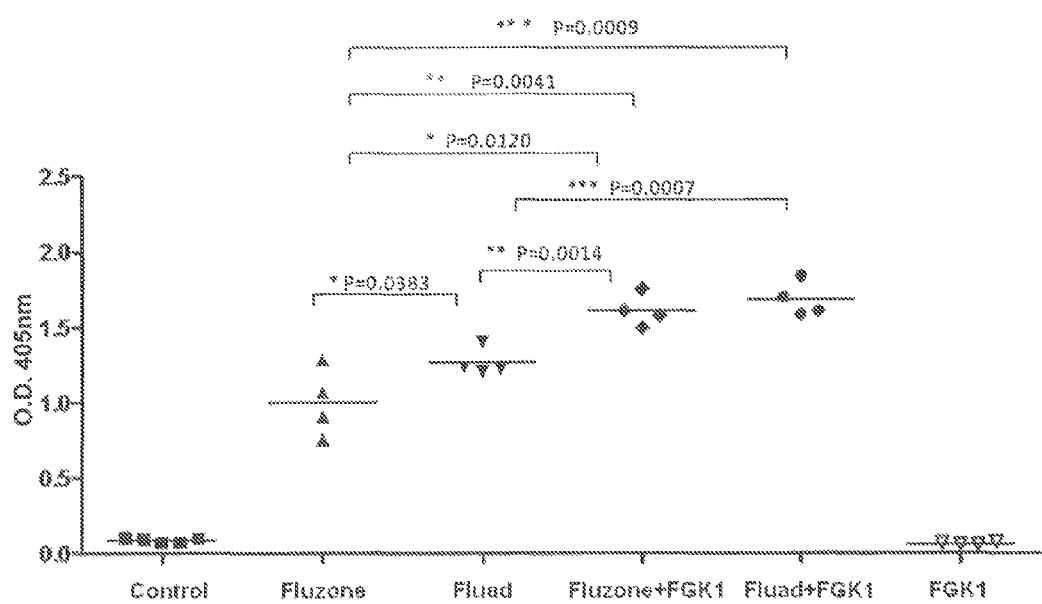
FIG. 6 shows the blood antibody (IgG) levels detected 45 days after immunization with the following treatments: 1. PBS as negative control group; 2. Human influenza vaccine FLUZONE®; 3. Human influenza vaccine FLUAD®; 4. Human influenza vaccine FLUZONE® plus FGK-1; 5. Human influenza vaccine FLUAD® plus FGK-1, and 6. FGK-1.

As shown on FIG. 6, 45 days after treatment inoculation the immune response induced by the adjuvant-containing commercial vaccine (FLUAD®) remains better than the immune response induced by FLUZONE® (adjuvant-free) commercial vaccine. However, when comparing the immune response induced co-administering both types of commercial vaccine (with or without adjuvant) and FGK-1, a higher immune response is elicited in all groups: first, it can be observed that when co-administering the FLUZONE® (adjuvant-free) influenza vaccine with FGK-1 and comparing the immune response elicited by FLUZONE® vaccine alone, a 60% higher antibody response is obtained when the vaccine is co-administered with FGK-1. Similarly, the immune response induced by co-administration of FLUZONE® vaccine with FGK-1 yields antibody levels 30% higher than those elicited by immunizing with FLUAD® vaccine (containing MF59 adjuvant) alone. When immunizing mice with FLUAD® vaccine (containing MF59 adjuvant) conjointly with FGK-1, 35% more antibodies are obtained with respect to those obtained by immunizing with FLUAD® vaccine alone. Additionally, the induced immune response by co-administering both FLUAD® and FLUZONE® with FGK-1 is similar to each other.

Example 7

Determination of the Response Induced by FGK-1 by Immunizing Pigs Intramuscularly To demonstrate the potentiating effect of FGK-1 on the immune response elicited by porcine influenza vaccine, four groups of male and female York/Landrace pigs, 2 months of age, were used. The following treatment schedules were administered to 10-pig groups:

Group 1: Pigs immunized with porcine influenza vaccine FLUSURE®, in the conditions directed by the manufacturer.
Group 2: Pigs immunized with porcine influenza vaccine FLUSURE®, a single dose plus FGK-1.
Group 3: Pigs immunized with porcine influenza vaccine FLUSURE®, in the conditions directed by the manufacturer plus FGK-1.

Porcine influenza vaccine was administered at a dose of 2 ml (as directed by the manufacturer), each consisting of two A type porcine influenza virus isolates subtypes H1N1 and H3N2. FLUSURE® vaccine for season 2009-2010 was used.

FGK-1 was used at titers of $2.5 \times 10^{12}$ phage units per pig, inactivated as detailed in this document, using a single dose per pig. Pigs received two FLUSURE® doses (as indicated by the manufacturer) per intramuscular route, and one dose of FGK-1 in the neck. The induced response was evaluated in plasma 30, 45, and 60 days after immunization.

Plasma was obtained from peripheral blood at the scheduled times after immunization, centrifuged at 2,500 rpm by 30 min, and aliquots were frozen until use.

Figure 7:
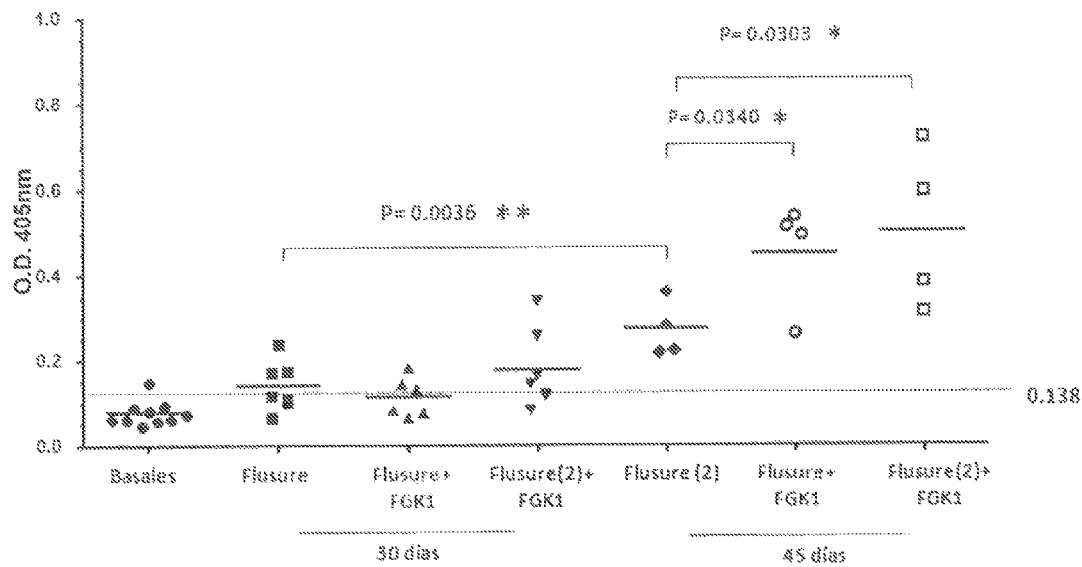
FIG. 7 shows IgG antibody levels detected in pig plasma 30 and 45 days after immunization with the following treatments: 1. Porcine influenza vaccine FLUSURE®; 2. Single-dose porcine influenza vaccine FLUSURE® plus FGK-1, and 3. Dual-dose porcine influenza vaccine FLUSURE® plus FGK-1.
Figure 8:
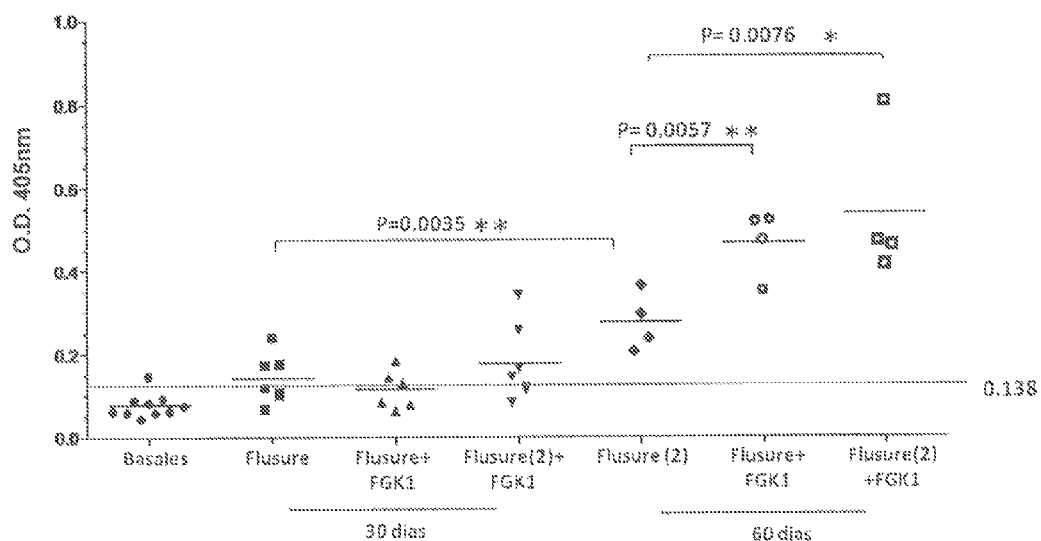
FIG. 8 shows IgG antibody levels detected in pig plasma 30 and 60 days after immunization with the following treatments: 1. Porcine influenza vaccine FLUSURE®; 2. Single-dose porcine influenza vaccine FLUSURE® plus FGK-1, and 3. Dual-dose porcine influenza vaccine FLUSURE® plus FGK-1.

As shown on FIGS. 7 and 8, single-dose immunization with porcine influenza vaccine induces a lower antibody response than that elicited after a second immunization with the same vaccine (as indicated by the manufacturer). This result becomes evident both at 15 days (a 94% increase) and at 30 days (a 96% increase) after the second immunization, corresponding to 45 and 60 days after the first immunization. When co-immunizing with influenza vaccine and FGK-1 according to the manufacturer directions (two doses of influenza vaccine), the antibody response elicited 15 days after the second immunization is increased by 84% with respect to the response induced by the influenza vaccine alone. However, when analyzing the antibody response induced 30 days after co-immunizing with influenza vaccine plus FGK-1 but using a single vaccine dose in co-immunization, it is observed that the induced response is 69% higher than the elicited antibody response after two administrations. This increase in the antibody response is sustained 30 days after the second immunization, showing a 94% increase when co-immunizing with the two vaccine doses, and a 69% increase when co-immunizing with a single vaccine dose.

In conclusion, these results demonstrate that GK-1 expression in phage (FGK-1) intramuscularly co-administered with porcine influenza vaccine according to the manufacturer directions induces a higher immune response than that elicited by the influenza vaccine alone. Additionally, it is demonstrated that co-immunizing with FGK-1 and the commercial vaccine, the latter in a lower dose than the ones indicated by the manufacturer, yields a better response than that induced by commercial vaccine under optimal conditions.

Example 8

Effect of FGK-1 to Improve the Humoral Immune Response Elicited by the Commercial Influenza Vaccine Fluzone® and the Commercial Influenza Vaccine with Adjuvant Fluad® Compared to the Immune Response Induced by S3Pvac-Phage To evaluate the potentiating effect of FGK-1 and S3Pvac-phage on the antibody response elicited by the two types of commercial human influenza vaccine, six groups of female BALB/cAnN mice, 7-8 weeks of age, were used. The following treatment schedules were evaluated:

Influenza vaccine was used at a dose of 1 µg/mouse of FLUZONE® vaccine [A/New Caledonia/20/99(H1N1) strain, A/Panama/2007/99(H3N2) strain (analogue to A/Moscow/10/99 strain), and B/Victoria/504/2000 strain (analogue to B/Sichuan/379/99 strain)] and 1 µg/mouse of FLUAD® influenza vaccine [A/Brisbane/59/2007 (H1N1) strain (analogue to A/Brisbane/59/2007, IVR-148 strain), A/Brisbane/10/2007(H3N2) strain (analogue to A/Uruguay/716/2007, NYMC X-175C strain), and B/FLORIDA/4/2006 strain]. FLUZONE® vaccine for the flu season 2008-2009, containing 45 µg of hemagglutinins per 0.5 ml-dose, and FLUAD® vaccine for the flu season 2008-2009, containing 45 µg of hemagglutinins and MF59C.1 adjuvant per 0.5 ml-dose, were used.

FGK-1 and M13 were used at titers of $10^{12}$ phage units per mouse. Mice received a single dose of each immunogen by subcutaneous route at the tail base, and the induced response was evaluated in serum at different times after immunization, namely 21 and 45 days after immunization.

Sera were obtained from peripheral blood, centrifuged at 5,000 rpm by 12 min, and aliquots were frozen until use.

Mice groups were segregated according to the immunization treatment they received, in the following way:

One group was immunized with PBS only, as negative control group. A second five-mouse group received adjuvant-free commercial influenza vaccine (FLUZONE®) only. The third five-mouse group received commercial influenza vaccine with adjuvant (FLUAD®). The fourth five-mouse group received adjuvant-free commercial influenza vaccine (FLUZONE®) co-administered with FGK-1. The fifth group received treatment with commercial influenza vaccine with adjuvant (FLUAD®) co-administered with FGK-1. Finally, the sixth five-mouse group received treatment with FGK-1 only.

Figure 9:
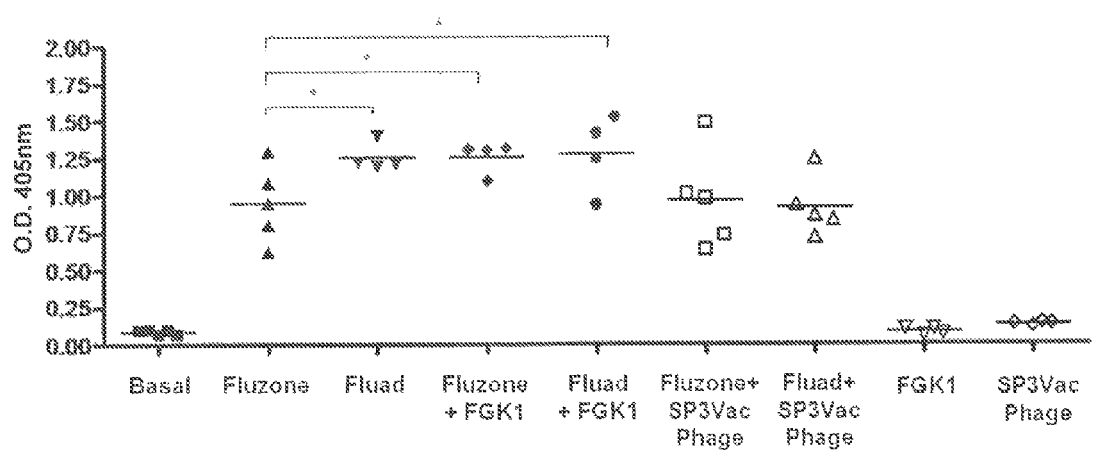
FIG. 9 shows IgG antibody levels detected in mouse serum 21 days after immunization with the following treatments: 1. Basal levels before immunization. 2. Human influenza vaccine FLUZONE®; 3. Human influenza vaccine FLUAD®; 4. Human influenza vaccine FLUZONE® plus FGK-1; 5. Human influenza vaccine FLUAD® plus FGK-1; 6. Human influenza vaccine FLUZONE® plus S3Pvac-phage; 7. Human influenza vaccine FLUAD® plus S3Pvac-phage; 8. FGK-1, and 9. S3Pvac-phage.

As shown on FIG. 9, since the day 21 after immunization an influenza antigen-specific IgG antibody response is elicited. However, it is apparent that commercial vaccine FLUAD® (containing adjuvant) elicits a higher antibody response with respect to that induced by adjuvant-free commercial influenza vaccine FLUZONE®. However, when comparing the effect induced by using FGK-1 co-administered with FLUZONE® vaccine, it is observed that the induced antibody levels are very similar to those induced by adjuvant-containing commercial vaccine, and this indicates that FGK-1 has a capacity of increasing the antibody levels in a similar extent to the adjuvant employed by the commercial vaccine. Nevertheless, when co-administering FGK-1 and commercial influenza vaccine containing adjuvant, a very similar immune response to that elicited by the sole administration of adjuvant-containing influenza vaccine is induced. On the other side, it is evident that co-administration of S3Pvac with commercial influenza vaccine (both FLUZONE® and FLUAD®) elicits a very similar immune response to the one induced by the commercial vaccine alone, since S3Pvac includes GK-1 in its composition. This induced response, however, is not higher than that elicited by co-administering the commercial influenza vaccine (both FLUZONE® and FLUAD®) with FGK-1, since the other S3Pvac components lack the capacity of immunopotentiating the response.

Figure 10:
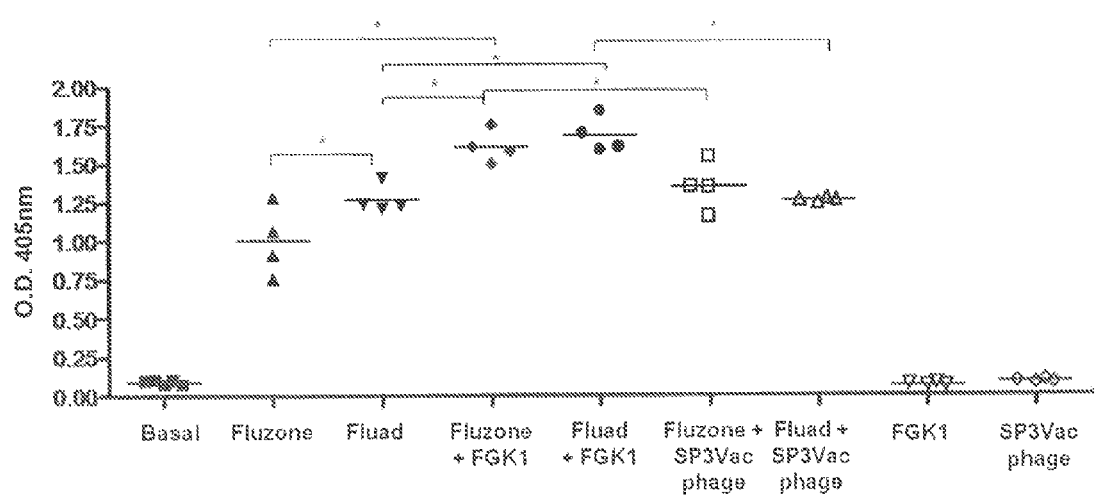
FIG. 10 shows IgG antibody levels detected in mouse serum 45 days after immunization with: 1. Basal levels before immunization. 2. Human influenza vaccine FLUZONE®; 3. Human influenza vaccine FLUAD®; 4. Human influenza vaccine FLUZONE® plus FGK-1; 5. Human influenza vaccine FLUAD® plus FGK-1; 6. Human influenza vaccine FLUZONE® plus S3Pvac-phage; 7. Human influenza vaccine FLUAD® plus S3Pvac-phage; 8. FGK-1, and 9. S3Pvac-phage.

As FIG. 10 shows, the immune response elicited 45 days after using commercial influenza vaccines which contain adjuvant or not (FLUAD® and FLUZONE®, respectively), and are co-administered with FGK-1 or S3Pvac-Phage to assess the immunopotentiator capacity of the latter, the following can be observed: Adjuvant-containing commercial influenza vaccine (FLUAD®) elicits a higher antibody level with respect to those induced by the adjuvant-free commercial influenza vaccine (FLUZONE®). However, it is very significant that at this time it is observed that co-administration of FGK-1 with the adjuvant-free commercial influenza vaccine elicits a significantly higher immune response than that induced by the adjuvant-containing commercial influenza vaccine; this result indicates that FGK-1 shows a higher capacity of potentiating the vaccine-induced response with respect to the adjuvant used in the commercial vaccine. It is noteworthy as well that co-administrating FGK-1 with the adjuvant-including commercial influenza vaccine elicits even higher antibodies than those induced by this adjuvant-including commercial influenza vaccine by itself; this shows that FGK-1 exhibits the capacity of potentiating the per se efficient response induced by the adjuvant-including commercial vaccine. Now, it is evident that S3Pvac-Phage co-administered with commercial influenza vaccines does not elicit a significant antibody increase with respect to the response induced by commercial vaccines alone. This indicates that S3Pvac-Phage does not show the immunopotentiating capacity exhibited by FGK-1.

This example demonstrates the immunopotentiating capacity of FGK-1 with respect to the response induced by two types of commercially available influenza vaccine, one adjuvant-free (FLUZONE®) and the other including adjuvant (FLUAD®). It also demonstrates that FGK-1 potentiates the specific immune response with higher efficiency than S3Pvac-phage vaccine.

The invention claimed is:

1. A method for potentiating humoral and cellular immunity in a human or an animal comprising co-administering an antigenic component derived from viral constituents, viral vaccines either attenuated, inactivated, or viral subunits and a pharmaceutical product comprising FGK-1 immunopotentiator, wherein FGK-1 is composed by GK-1 peptide, constituted by the 18-amino acid sequence G-Y-Y-Y-P-S-D-P-N-T-F-Y-A-P-P-Y-S-A (SEQ ID NO: 1) linked to the pVIII surface protein of M13 filamentous phage.

2. The method according to claim 1, wherein the antigenic component is a vaccine against influenza virus.

3. The method according to claim 1, wherein the pharmaceutical product is administered by intranasal route.

4. The method according to claim 1, wherein the pharmaceutical product is administered by subcutaneous route.

5. The method according to claim 1, wherein the pharmaceutical product is administered by intramuscular route.

* * * * *

SEQUENCE LISTING

```
<160> NUMBER OF SEQ ID NOS: 4

<210> SEQ ID NO 1
<211> LENGTH: 18
<212> TYPE: PRT
<213> ORGANISM: Taenia solium

<400> SEQUENCE: 1

Gly Tyr Tyr Tyr Pro Ser Asp Pro Asn Thr Phe Tyr Ala Pro Pro Tyr
1               5                   10                  15

Ser Ala

<210> SEQ ID NO 2
<211> LENGTH: 18
<212> TYPE: PRT
<213> ORGANISM: Artificial Sequence
<220> FEATURE:
<223> OTHER INFORMATION: GK-1 peptide sequence of amino acids 69-85

<400> SEQUENCE: 2

Gly Tyr Tyr Tyr Pro Ser Asp Pro Asn Thr Phe Tyr Ala Pro Pro Tyr
1               5                   10                  15

Ser Ala

<210> SEQ ID NO 3
<211> LENGTH: 57
<212> TYPE: DNA
<213> ORGANISM: Artificial Sequence
<220> FEATURE:
<223> OTHER INFORMATION: Synthetic oligonucleotides (invitrogent) 5'GK1

<400> SEQUENCE: 3
aattaggtta ttactatcct atctgatcca aataccttct acgctccacc ctacagc      57

<210> SEQ ID NO 4
<211> LENGTH: 56
<212> TYPE: DNA
<213> ORGANISM: Artificial Sequence
<220> FEATURE:
<223> OTHER INFORMATION: synthetic oligonucleotides (Invitrogen) 3'GK1

<400> SEQUENCE: 4
gatcgctgta gggtggagcg tagaaggtat ttggatcaga tggatagtaa taacct       56
```